United States Patent [19]
Fleenor et al.

[11] Patent Number: 5,484,435
[45] Date of Patent: Jan. 16, 1996

[54] BIPOLAR ELECTROSURGICAL INSTRUMENT FOR USE IN MINIMALLY INVASIVE INTERNAL SURGICAL PROCEDURES

[75] Inventors: Richard P. Fleenor, Englewood; Robert L. Bromley, Louisville, both of Colo.

[73] Assignee: Conmed Corporation, Utica, N.Y.

[21] Appl. No.: 149,183

[22] Filed: Nov. 8, 1993

Related U.S. Application Data

[63] Continuation-in-part of Ser. No. 821,753, Jan. 15, 1992, abandoned.

[51] Int. Cl.⁶ .................................................... A61B 17/39
[52] U.S. Cl. ............................. 606/46; 606/48; 606/50
[58] Field of Search .......................... 606/46, 48, 50, 606/51

[56] References Cited

U.S. PATENT DOCUMENTS

| | | | |
|---|---|---|---|
| 2,056,377 | 10/1936 | Wappler | 128/303.14 |
| 2,618,267 | 11/1952 | Hanriot | 128/303.14 |
| 2,708,933 | 5/1955 | August | 128/303.14 |
| 2,828,747 | 4/1958 | August | 128/303.14 |
| 3,434,476 | 3/1969 | Shaw et al. | 606/22 |
| 3,562,486 | 2/1971 | Hatch | 219/121.52 |
| 4,040,426 | 8/1977 | Morrison, Jr. | 128/303.17 |
| 4,060,088 | 11/1977 | Morrison, Jr. et al. | 219/121.51 |
| 4,116,198 | 9/1978 | Roos | 128/303.15 |
| 4,562,838 | 1/1986 | Walker | 128/303.14 |
| 4,719,914 | 1/1988 | Johnson | 606/45 X |
| 4,781,175 | 11/1988 | McGreevy et al. | 128/303.17 |
| 4,901,719 | 2/1990 | Trenconsky et al. | 606/49 |
| 4,911,159 | 3/1990 | Johnson et al. | 606/45 X |
| 5,047,027 | 9/1991 | Rydell | 606/48 |
| 5,085,659 | 2/1992 | Rydell | 606/47 |

FOREIGN PATENT DOCUMENTS 3423-356-A  2/1986  Germany.

OTHER PUBLICATIONS

"Berchtold 'BiCut–System'" by Berchtold GmbH & Co.

*Primary Examiner*—Lee S. Cohen
*Attorney, Agent, or Firm*—Sheridan Ross & McIntosh

[57] ABSTRACT

A bipolar electrosurgical instrument for use in laparoscopic surgery or other minimally invasive internal surgical procedures is disclosed. In one embodiment, a bipolar electrosurgical apparatus (10) is provided which is suitable for laparoscopic applications. The apparatus (10) comprises an active electrode (18) and a current return electrode shoe (34). A spring (44) or other resilient member urges the shoe (34) into tissue contact when the active electrode (18) is positioned for surgery. In another embodiment, an axially retractable active electrode (90) is used to grip tissue and draw the tissue back to a passive electrode (92) The apparatus of the present invention is capable of functioning in cutting, coagulation and desiccation modes.

14 Claims, 7 Drawing Sheets

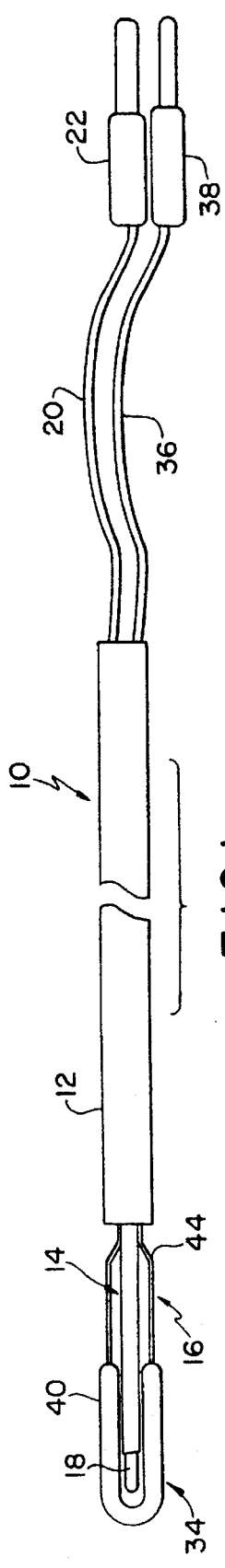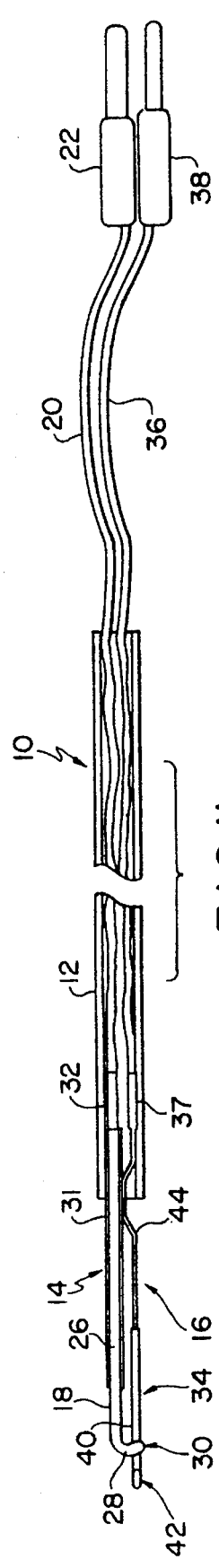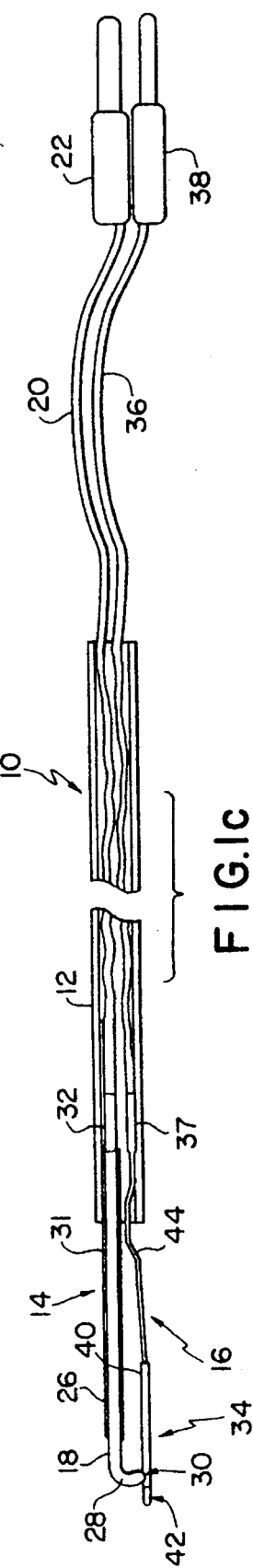

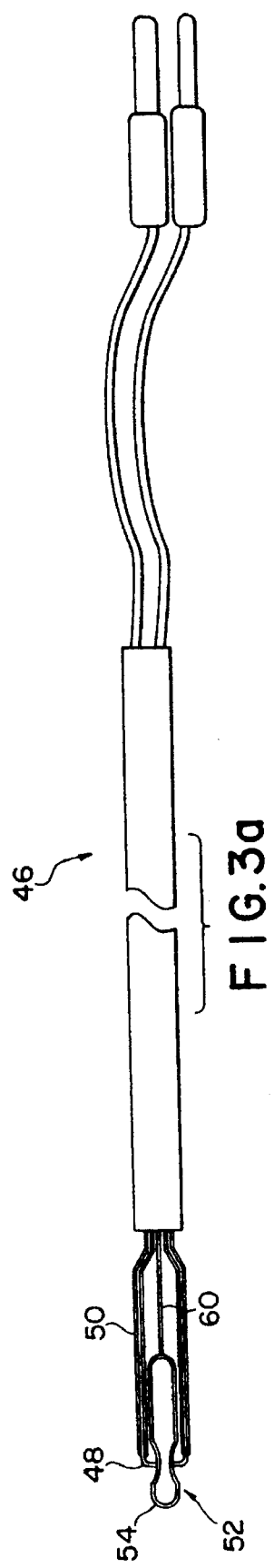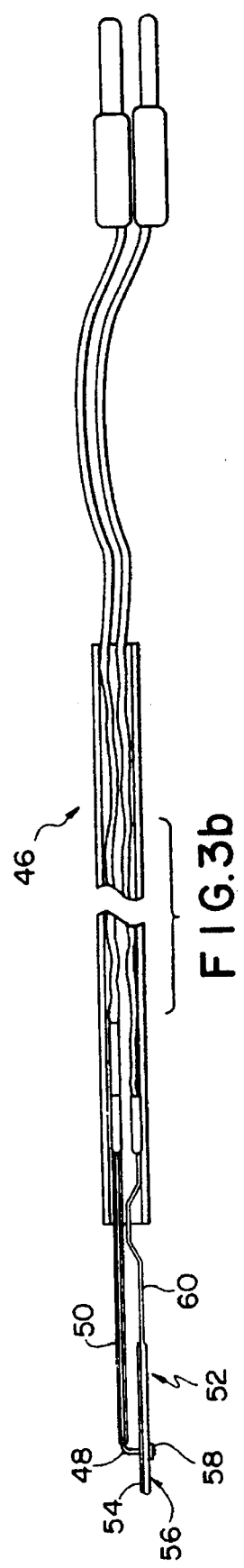

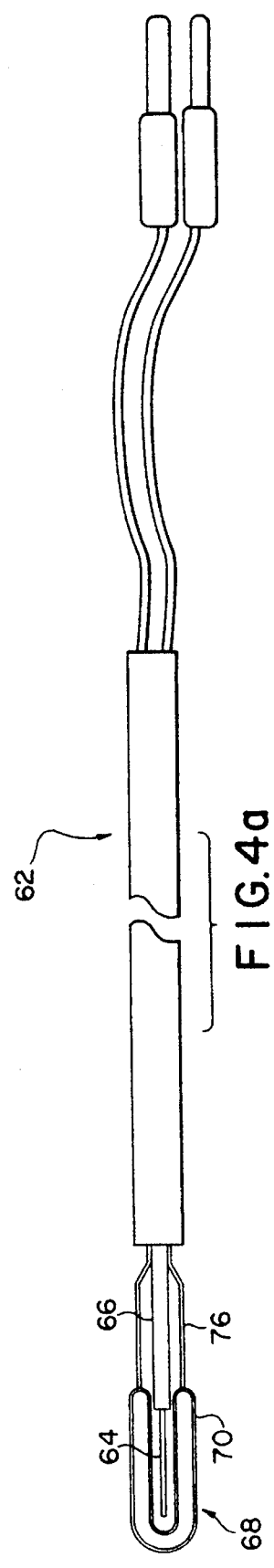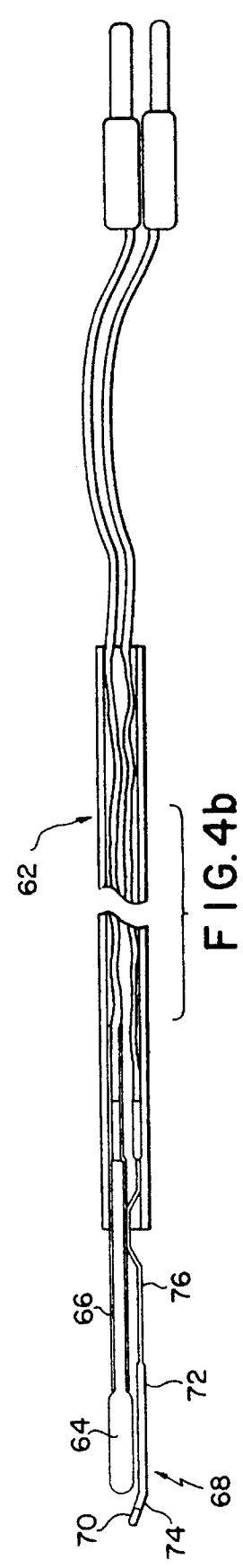

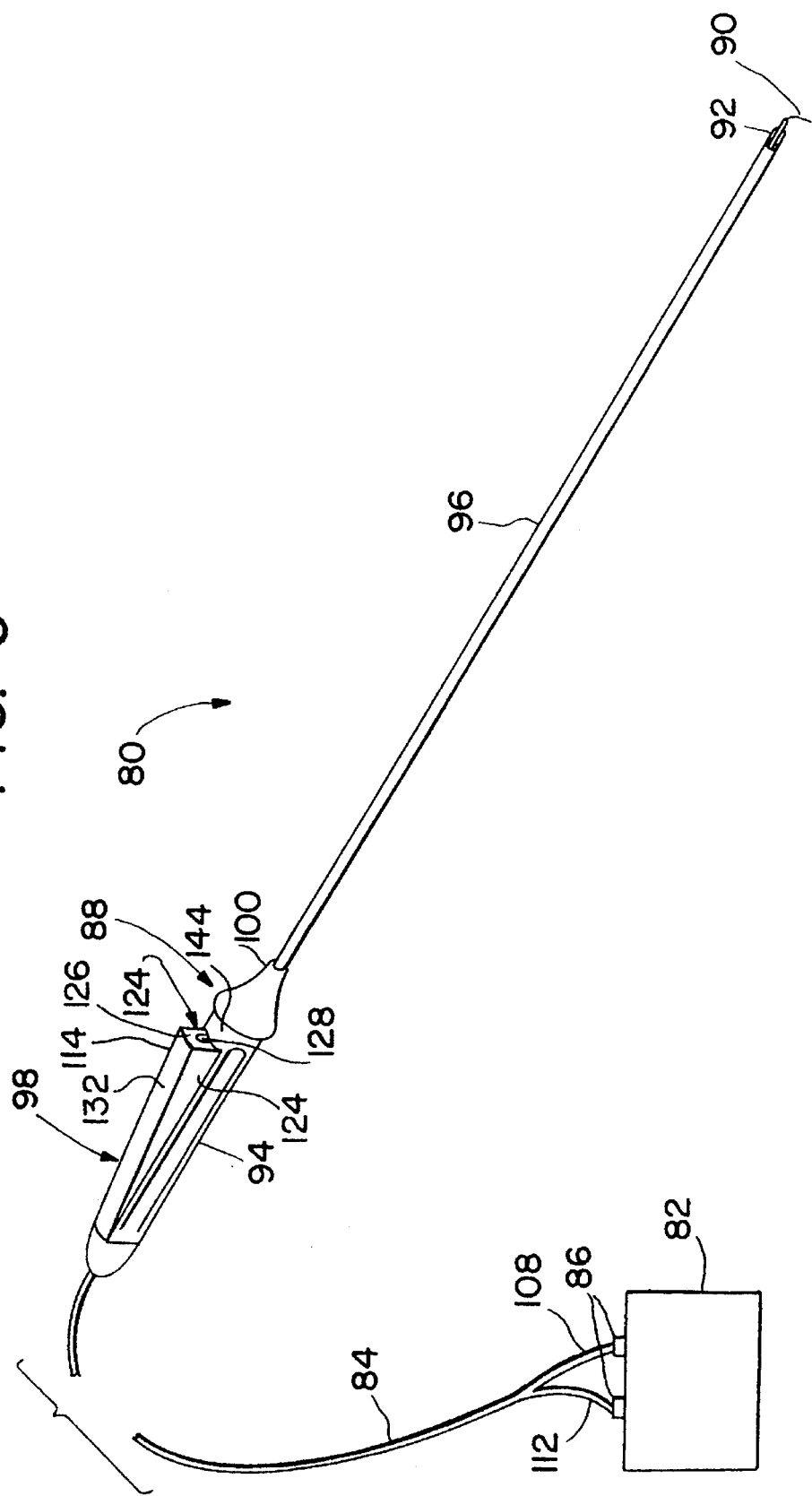

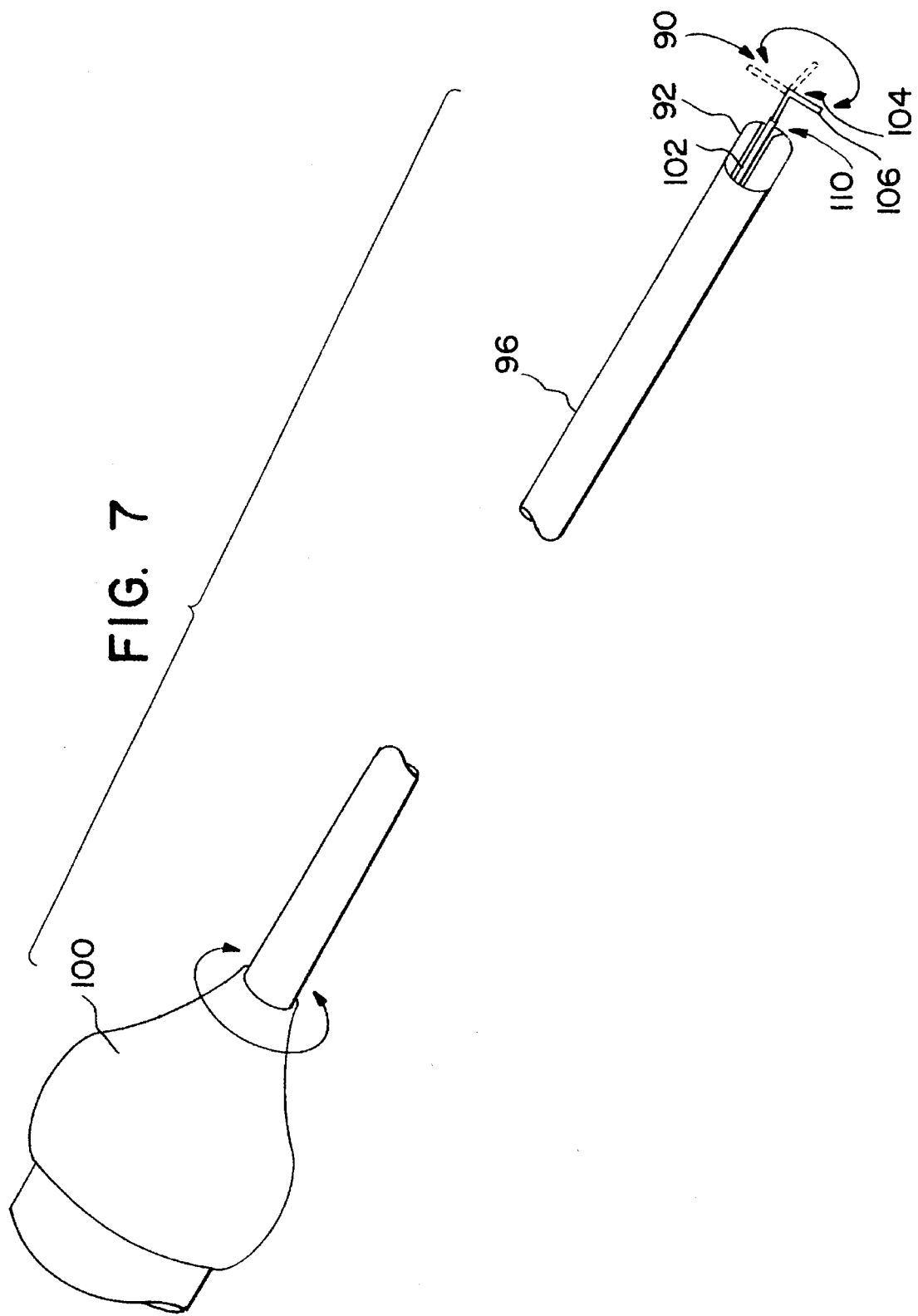

BIPOLAR ELECTROSURGICAL INSTRUMENT FOR USE IN MINIMALLY INVASIVE INTERNAL SURGICAL PROCEDURES

This application is a continuation-in-part of U.S. patent application Ser. No. 07/821,753 entitled "BIPOLAR ELECTROSURGICAL INSTRUMENT", filed on Jan. 15, 1992, now abandoned.

FIELD OF THE INVENTION

This invention relates generally to electrosurgical instruments and, in particular, to a bipolar electrosurgical instrument capable of use for cutting, coagulation and desiccation. The instrument of the present invention is particularly adapted for use in minimally invasive internal procedures such as laparoscopic surgery.

BACKGROUND OF THE INVENTION

Electrosurgery involves the use of an RF signal to produce electrosurgical effects, e.g., to cut, coagulate and/or desiccate. In conventional monopolar electrosurgery, an active electrode is contacted or positioned in close proximity to the tissue to be treated and a current return means (i.e. a pad) is positioned in contact with the patient to complete the circuit. Near the tip of the active electrode, the current is concentrated through a small area of tissue to provide a current density sufficient for cutting or coagulation. The current return means maintains a relatively large area of tissue contact to avoid tissue damage. If the contact surface of the current return means is too small, the current density may result in tissue damage.

In recent years, bipolar instruments have been used in certain electrosurgical applications. Bipolar instruments include a pair of closely spaced electrodes of opposite polarity, thereby eliminating the need for a remotely located current return means. It is an advantage of bipolar electrosurgical instruments that current flow is substantially restricted to a small area between the electrodes. Bipolar instruments thereby reduce the likelihood of current damage due to high local current densities or current flow through highly sensitive tissues. Thus, bipolar instruments are advantageously employed in applications such as neurosurgery where the adjacent tissue may be particularly susceptible to damage. Further ease-of-use advantages can be readily appreciated since bipolar instruments do not entail interconnection of a remotely located current return means.

Despite these advantages, bipolar instruments have suffered certain limitations. For example, certain bipolar instruments are not unitary, i.e., the electrodes are mounted on separate support structures. Surgeons using such instruments commonly operate one electrode with each hand. Such instruments, therefore, have the disadvantage that the surgeon may be left without a free hand during surgery. In addition, the use of two separate support structures may crowd the surgical site and limit the surgeon's view. Such instruments are also difficult to use in constricted areas and may therefore necessitate larger incisions.

Another limitation of known bipolar instruments is that such instruments may fail to reliably maintain electrode/tissue contact during surgery. In some known bipolar instruments, both of the electrodes are rigidly interconnected to a single support structure such that substantially constant spacing is maintained between the electrodes. When such instruments are used in an area of irregular tissue topography, one or both of the electrodes may occasionally lose contact with the tissue due to the inability to move the electrodes independently, resulting in unsatisfactory instrument performance.

Similarly, certain bipolar instruments have been limited due to the inability to easily and adequately adjust the cutting depth of such instruments during surgery. For example, one type of bipolar instrument employs a single cutting electrode and a second current return means positioned a substantially fixed distance rearwardly of the cutting electrode. In practice, a surgeon's ability to control the cutting depth of such instruments is hampered due to the inability to easily vary the distance between the cutting electrode and the current return means during surgery.

In addition, known bipolar instruments have generally not been adapted for general use in cutting, coagulation and desiccation modes. The electrosurgical effect achieved can be varied by changing the signal provided by an electrosurgical generator. For example, a continuous sinusoidal signal waveform generally is used for cutting while an interrupted waveform is used for coagulation. Presently, many bipolar instruments are principally employed to coagulate using the interrupted coagulation signals. Indeed, electrosurgical generators often have separate outlets for interfacing with monopolar and bipolar instruments and the cut signal option is often not even available via the bipolar outlet. It is therefore common for surgeons to use separate instruments for cutting and coagulation, resulting in time consuming double handling during surgery. Other bipolar instruments produce electrosurgical effects at both of the electrodes, thereby affecting the surgeon's ability to accurately limit the area of tissue to be acted upon.

Moreover, many challenges remain with respect to realizing the full potential of bipolar electrosurgical instruments for minimally invasive internal surgical procedures such as laparoscopic surgery. Such minimally invasive procedures, which normally involve accessing the surgical site through a narrow tube or cannula, are increasingly popular because they can avoid the need for large incisions, thereby reducing patient scarring and trauma. However, the spatial limitations inherent in such settings place practical limits on the dimensions and configuration of the electrodes utilized and can make it difficult to maintain adequate electrode/tissue contact for certain procedures. Additionally, in designing electrosurgical instruments for use in such constricted environments, special care must be taken to reduce the likelihood of producing undesired electrosurgical effects due to inadvertent tissue contact, e.g., inadvertent contact between exposed active electrode portions and tissue adjacent to the surgical site. A further consideration in designing such instruments is that the surgeon's view of the surgical site, which is typically limited during minimally invasive internal procedures, should not be unduly obstructed. Presently, it appears that no one has succeeded in providing a bipolar electrosurgical instrument for use in a variety of minimally invasive procedures which meets the needs of the industry.

SUMMARY OF THE INVENTION

The present invention is directed to a bipolar electrosurgical instrument which is particularly adapted for use to perform various minimally invasive internal surgical procedures. The instrument of the present invention can operate in cutting, coagulation and desiccation modes, thereby reducing the need to switch instruments during surgery and simplifying certain procedures. Moreover, during operation in such modes, the electrosurgical effects are substantially restricted to a small area adjacent a single active electrode whereas the other electrode remains passive, thus avoiding undesired electrosurgical effects or fouling of the instrument. The instrument of the present invention also reliably maintains electrode/tissue contact during surgery so as to enhance instrument performance. In addition, the instrument of the present invention allows a surgeon to control the relative positioning of the active and passive electrodes during surgery, for example, to regulate cutting depth or minimize the region of current flow. Furthermore, the present invention allows the surgeon to engage or grip tissue with the electrodes positioned in a first arrangement, e.g., for enhanced viewing, and then apply the electrosurgical signal with the electrodes positioned in a second arrangement as may be desired.

According to one aspect of the present invention, the bipolar electrosurgical instrument comprises an instrument body, an active electrode, a passive electrode and a mechanism for positioning the active and/or passive electrodes such that the electrodes can be positioned in a first arrangement in preparation for performing a surgical procedure, e.g., for engaging the instrument with the tissue to be acted upon, and a second arrangement for performing the procedure. The instrument body includes a hand-held portion and an elongated, substantially rigid portion for insertion through an access cannula to an internal surgical site. In this manner, the surgeon can accurately control the positioning of the electrodes via forward, rearward, and/or transverse manipulation of the instrument. Both the active electrode and the passive electrode extend forwardly from a front end of the elongated portion of the instrument body. The active electrode, which includes an insulated portion and an exposed active tissue contact surface, is capable of transmitting at least cut and coagulate signals. The passive electrode has a passive tissue contact surface which has a greater area than the active tissue contact surface such that substantially no electrosurgical effects are produced adjacent thereto. Preferably, the passive tissue contact surface area is at least about three times as great as the active tissue contact surface area.

The positioning mechanism allows the relative positioning of the active and passive electrodes to be adjusted after the electrodes have been inserted through the cannula to the surgical site. This can be accomplished by moving the active electrode, the passive electrode or both. In addition, the electrode(s) can be moved axially or transversely relative to the access cannula and the generally aligned elongated instrument body portion. In one embodiment, the passive electrode is transversely deflectable relative to the active electrode. For example, the passive electrode can be formed from a conductive leaf spring resiliently mounted on the instrument housing or the passive electrode can be hingedly mounted thereon. Preferably, the passive electrode is biased away from the active electrode by a spring or other resilient member. In this manner, the passive electrode is urged against the tissue to be acted upon for reliable tissue/electrode contact when the active electrode is pressed into contact with the tissue to perform a surgical procedure. In another embodiment, the active electrode can be moved axially towards or away from the passive electrode, i.e., between retracted and extended positions, respectively. The surgeon can conveniently actuate such movement, for example, via a lever, button or the like provided on the hand-held portion. Preferably, the active electrode is biased towards the extended position for enhanced viewing as the active electrode is positioned for surgery.

According to another aspect of the present invention, tissue is gripped with the active and passive electrodes positioned in a first arrangement, and moved as the electrodes are positioned in a second arrangement for conducting an electrosurgical procedure. For example, the tissue can be gripped with the electrodes positioned in a widely separated arrangement for enhanced viewing. Thereafter, the electrodes can be drawn more closely together, e.g., to ensure adequate tissue contact or limit the region of current flow through the tissue. In one embodiment, the active electrode comprises a hook portion for grippingly engaging the tissue. The active electrode is axially moveable between an extended position where the active electrode is positioned forwardly of the passive electrode and a retracted position where the active and passive electrodes are substantially nested.

BRIEF DESCRIPTION OF THE DRAWINGS

For a more complete understanding of the present invention and further advantages thereof, reference is now made to the following Detailed Description of the Invention, taken in conjunction with the Drawings, in which:

FIG. 1a is a top view of an electrosurgical apparatus constructed in accordance with an embodiment of the present invention;

FIG. 1b is a side cross-sectional view of the apparatus of FIG. 1a in a deflected position;

FIG. 1c is a side cross-sectional view of the apparatus of FIG. 1a in a relaxed position;

FIG. 3a is a top view of an electrosurgical apparatus constructed in accordance with an alternative embodiment of the present invention;

FIG. 3b is a side cross-sectional view of the apparatus of FIG. 3a;

FIG. 4a is a top view of an electrosurgical apparatus constructed in accordance with a further alternative embodiment of the present invention;

FIG. 4b is a side cross-sectional view of the apparatus of FIG. 4a;

FIG. 5 is a perspective view of a bipolar electrosurgical instrument constructed in accordance with a still further embodiment of the present invention;

FIG. 7 illustrates the electrode swivel feature of the instrument of FIG. 5;

DETAILED DESCRIPTION

Figure 2:
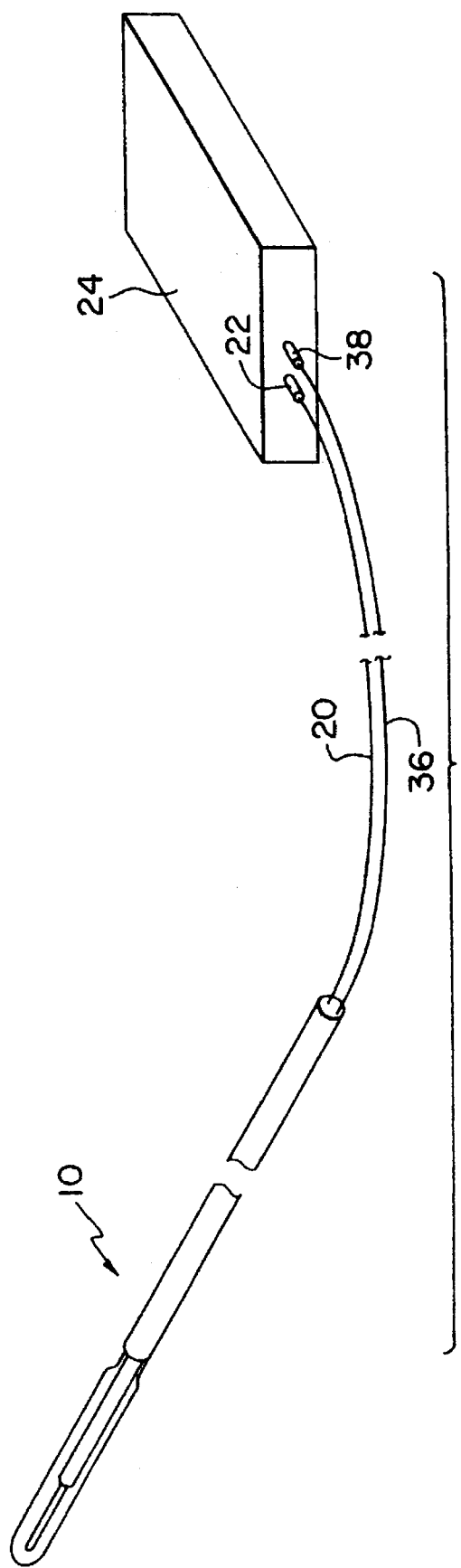
FIG. 2 is a perspective view of the apparatus of FIG. 1 interconnected with an electrosurgical generator.
Figure 6:
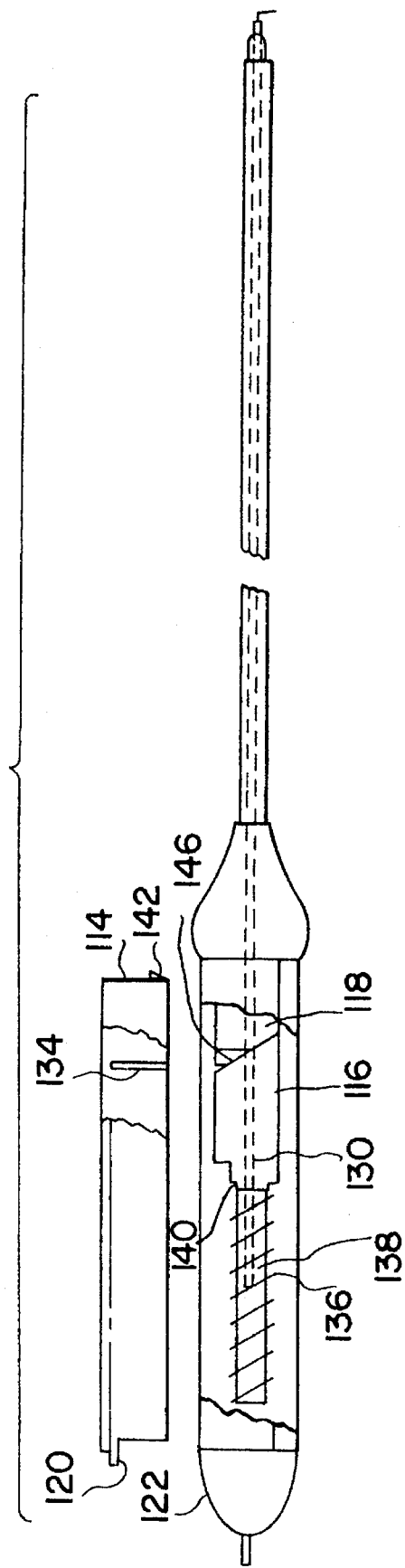
FIG. 6 is a side view partially cut-away of the instrument of FIG. 5.
Figure 8B:
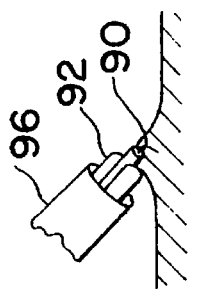
FIG. 8b is a perspective view of an end portion of the instrument of FIG. 5 in a retracted position.
Figure 8A:
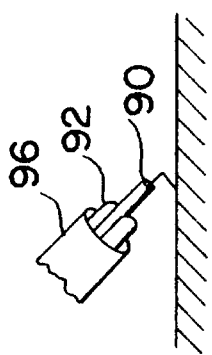
FIG. 8a is a perspective view of an end portion of the instrument of FIG. 5 in an extended position.

In FIGS. 1–2, like items are identified by like and corresponding numerals for ease of reference. Referring to FIGS. 1a–1c, a bipolar electrosurgical apparatus constructed in accordance with an embodiment of the present invention is generally identified by the reference numeral 10. FIGS. 1a–1c show a top view of the apparatus 10 (FIG. 1a), a side view of the apparatus 10 in a deflected position (FIG. 1b), and a side view of the apparatus 10 in a relaxed position (FIG. 1c).

The apparatus 10 comprises a longitudinal apparatus housing 12 which is interconnected to an active electrode assembly 14 and a current return electrode assembly 16. The housing 12 may be of molded plastic construction and may include a portion which is contoured for optimal handling by a user. In the illustrated embodiment, the housing comprises an elongated, substantially rigid plastic tube having an outside diameter selected to allow the housing 12 to be at least partially inserted through an access cannula for laparoscopic surgery.

The active electrode assembly 14 includes an active electrode 18 and signal supply wire 20 which terminates in standard plug 22 for electrically interconnecting the electrode 18 to a standard electrosurgical generator 24 (FIG. 2). It will be appreciated that the plug 22 can be of a type suitable for interconnection to the generator outlet normally utilized by monopolar instruments. The electrode 18 may be of various configurations depending, for example, on the intended application. Thus, the illustrated electrode 18 can be employed for localized cutting and/or coagulating. A so-called hoop electrode such as shown in FIGS. 3a and 3b may be preferred to remove blockage from passageways, e.g., in transurethral surgery. Similarly, a generally blade-shaped electrode such as shown in FIGS. 4a and 4b may be preferred for making longitudinal incisions.

As shown in FIGS. 1a–1c, the electrode 18 is generally hook-shaped having a longitudinal portion 26 and a transverse portion 28. A relatively small end surface 30 is thereby provided so that the electrosurgical effects are restricted to a small tissue area. Insulation 31 is provided about a portion of electrode 18 to reduce the likelihood of shunting or short circuits between electrode 18 and return assembly 16. The electrode 18 may be removably interconnected to the wire 20 by way of a socket 32 to facilitate replacement of the electrode 18.

The return electrode assembly 16 comprises an electrode shoe 34 and a current return wire 36 which terminates in standard plug 38 for electrically interconnecting shoe 34 to a standard electrosurgical generator 24 (FIG. 2). The shoe 34 may be removably interconnected to wire 36 by way of socket 37. The shoe 34, which is partially covered by insulation 40 to prevent shunts or short circuits, includes an exposed tissue contact surface 42. In the illustrated embodiment, the surface 42 is generally "U" shaped and is disposed around the electrode 18 to enhance tissue contact, particularly in areas of irregular tissue topography.

In order to achieve satisfactory performance and avoid tissue damage, shoe 34 must maintain an adequate area of tissue contact. It will be understood that the area of tissue contact necessary to avoid harmful current densities will depend on a number of factors including the power supplied to apparatus 10 and the rate of movement of the shoe 34. The apparatus 10 can be advantageously employed in certain low power (10 to 35 watts), narrow surgical applications, e.g., laparoscopic surgery. In such a setting, the shoe 34 should maintain an area of tissue contact at least three times that of the active electrode 18. Such an area of tissue contact performs adequately under conditions wherein the shoe 34 is frequently moved, avoids excessive obstruction of the surgeon's view and allows the apparatus 10 to be sized appropriately for laparoscopic applications. Of course, the required area of tissue contact will be greater for higher power applications and for applications where the shoe 34 is moved infrequently.

The electrode 18 and the shoe 34 are interconnected to the housing 12 in a manner such that the shoe 34 and contact surface 42 are urged into tissue contact when the electrode 18 is positioned for surgery. For example, a spring or other resilient member may be disposed between the assemblies 14 and 16 so that the shoe 34 is urged into tissue contact when the electrode 18 is positioned for surgery. In the illustrated embodiment, the shoe 34 is interconnected to the housing 12 by way of an integral or interconnected conductive leaf spring 44 (which additionally serves to electrically interconnect shoe 34 and wire 36). The spring 44 allows for relative movement between the active electrode 18 and electrode shoe 34. It will be appreciated that many other configurations and assemblies for maintaining return electrode/tissue contact are possible according to the present invention. For example, shoe 34 could be pivotally mounted on housing 12 and a coil spring or other resilient member could be disposed between the electrode 18 and shoe 34 to urge the electrode 18 and shoe 34 laterally apart. Similarly, for applications wherein the return electrode is longitudinally retracted when the active electrode is positioned for surgery, a resilient member could be provided to urge the return electrode towards a longitudinally extended position.

Referring to FIG. 2, standard plug 22 of signal supply wire 20 and standard plug 38 of current return wire 36 are interconnected with standard electrosurgical generator 24 for use with apparatus 10. It is an advantage of the present invention that the apparatus 10 can be interconnected to the generator outlet normally utilized by monopolar instruments. By way of example only, electrosurgical generator 24 may be any of the following or equivalents thereof: the "ACC 450," "ACC 470" or "MCC 350" of Erbe Electro Medical Equipment; the "FORCE 2" or "FORCE 4" generators of Vallylab, Inc.; the "EMS 3000," "EMS 4400," or "EMS 5000" of Bard Electro Medical Systems, Inc., the "X10" of Bovi, Inc.; the "9000" by Concept, Inc.; or the "EXCALIBER," "MH 380" or "MH 450" of Aspen Laboratories, Inc. These products are designed to receive standard plugs 22 and 38, and can be preset to selectively provide at least an appropriate first predetermined RF signal for tissue cutting and an appropriate second predetermined RF signal for coagulation. Generally, it is also possible to use these products for desiccation. Again, caution must be exercised in matching a generator or generator setting with a particular instrument and application as the required area of return electrode/tissue contact depends on factors including the power supplied to the instrument and rate of return electrode movement.

The apparatus 10 can be employed in laparoscopic surgery as follows. First, the surgeon makes a small incision to allow insertion of an access cannula. The access cannula, which may be provided at its leading edge with a trocar, is then inserted into the patient to provide access to the surgical site. Thereafter, the electrode 18 and shoe 34 are inserted through the access cannula to the surgical site. The surgeon positions the electrode 18 for surgery with the aid of an optical system. To initiate a surgical procedure, the surgeon moves the electrode 18 towards the tissue to be treated, or downwardly as viewed in FIGS. 1b and 1c. The shoe 34, which contacts the tissue first, deflects as shown in FIG. 1b to allow the electrode 18 to be positioned for surgery. In a cutting mode, the cutting depth can be adjusted by simply pressing the instrument harder against the tissue such that greater deflection is achieved. During surgery, the spring 44 urges the shoe 34 against the tissue so that adequate tissue contact is maintained. It will be appreciated that shoe 34 must maintain a sufficient area of tissue contact to function in a cut or coagulation mode substantially without cutting or burning of the tissue adjacent to the shoe 34 or attendant fouling of the shoe 34.

Referring to FIGS. 3a and 3b, top and side views, respectively, of apparatus 46 constructed in accordance with an alternative embodiment of the present invention are shown. The apparatus 46 is provided with a so-called hoop electrode 48, such as is commonly employed for transurethral surgery. The electrode 48 is partially covered by insulation 50 to prevent shunts or short circuits between the hoop electrode 48 and current return electrode shoe 52. Similarly, insulation 54 is provided on a top portion of the shoe 52 to prevent shunts or short circuits. A bottom surface 56 of the shoe 52 is exposed to provide a tissue contact area.

When the electrode 48 is in a retracted position (shown), the electrode 48 rests against an insulation pad 58 provided on the bottom surface 56 of current return electrode shoe 52. As the electrode 48 is positioned for surgery, shoe 52 is deflected such that electrode 48 pulls away from pad 58. The bottom surface 56 of the shoe 52 is urged into contact with tissue during surgery by spring 60.

Referring to FIGS. 4a and 4b, top and side views, respectively, of a apparatus constructed in accordance with a further alternative embodiment of the present invention are shown. The apparatus 62 includes a generally blade-shaped active electrode 64. Again, insulation 66 is provided about a portion of the electrode to reduce the likelihood of shunts or short circuits between the electrode 64 and the current return electrode shoe 68. Insulation 70 is also provided on a top portion of the shoe 68 to reduce the likelihood of shunts or short circuits. However, a bottom surface 72 of the shoe 68 is exposed for tissue contact. The shoe 68 and bottom surface 72 are generally "U" shaped and are disposed around the electrode 64 to enhance tissue contact, particularly in areas of irregular tissue topography. In addition, a front portion of the shoe 68 may be slanted upwardly, as shown, to enhance tissue contact when the apparatus 62 is employed in an angled position as is common for making incisions. As the electrode 64 is positioned for surgery, the shoe 68 is deflected such that the electrode 64 extends therethrough. Spring 76 urges the bottom surface 72 into tissue contact when the electrode 64 is thus positioned for surgery.

Referring to FIGS. 5–8b, a bipolar electrosurgical instrument 80 constructed in accordance with a still further embodiment of the present invention is shown. As shown in FIG. 5, the instrument 80 is connected to a standard electrosurgical generator 82 via electrical wires 84 and standard plugs 86 as described above. Like the embodiments described above, the instrument 80 can be interconnected to generator outlets normally utilized by monopolar instruments to perform cutting, coagulation and desiccation procedures as desired.

Generally, the instrument 80 comprises a housing 88, a hook-shaped active electrode 90 and a generally semispherical shaped passive electrode 92. The housing 88, which may be formed from molded, substantially rigid plastic, includes a hand-held portion 94 and an elongated tubular portion 96. In addition, the housing 88 includes a lever assembly 98 for extending and retracting the active electrode 90, and a swivel joint 100 for rotatably interconnecting the hand-held portion 94 and tubular portion 96, as will be described in detail below.

The active electrode 90, which is formed from conductive metallic material partially sheathed in insulating material 102 such as Kevlar or one of various ceramic insulators, includes an exposed portion 104 terminating in hooked tip 106. As will be appreciated upon consideration of the description below, the hooked tip 106, in addition to transmitting an electrosurgical signal to the tissue, is also used to frictionally engage or slightly puncture the tissue so that the tissue can be drawn rearwardly into firm contact with the passive electrode 92.

Passive electrode 92, which is preferably formed from conductive metallic material, includes a slit 110 for receiving the active electrode tip 106 and tissue therein when the active electrode is in a retracted position as described below. In this manner, the tissue is firmly engaged to ensure reliable tissue/electrode contact, the surface area of tissue/electrode contact is increased and the region of tissue exposed to electrical current flow is minimized. Passive electrode 92 is electrically interconnected to generator 82 via lead 112.

During surgery, it may be desirable to change the angular orientation of the active electrode tip 106, for example, to facilitate approaching tissue from the bottom, top, side, etc. However, it is generally not convenient to rotate the entire housing because such rotation could inhibit convenient thumb or finger access to the lever assembly 98. Accordingly, in the illustrated embodiment, swivel joint 100 is provided to accommodate rotation of the electrodes 90 and 92 without rotating hand-held portion 94 of housing 88. In this regard, the electrodes 90 and 92 are mounted to rotate in unison with the tubular portion 96 of housing 88 which, in turn, is mounted on swivel joint 100. Swivel joint 100 is rotatably mounted on the hand-held portion 94 of housing 88. The surgeon can thus rotate the electrodes 90 and 92 without rotating hand-held portion 94 by grasping the swivel joint 100 and turning the joint 100 (as shown in FIG. 7) relative to hand-held portion 94.

An additional feature of the instrument 80 relates to the ability to move the active electrode 90 between an extended position (FIG. 8a) for enhanced viewing when engaging tissue and a retracted position (FIG. 8b) for enhanced instrument performance when producing the desired electrosurgical effects. In the illustrated embodiment, movement of the active electrode 90 is accomplished by deploying lever assembly 98. Component parts of lever assembly 98 are shown in the perspective view of FIG. 5 and the partial cut-away view of FIG. 6. The assembly 98 comprises lever 114 (shown separated from hand-held portion 94 in FIG. 6 for clarity of illustration), active electrode mount 116 and passive electrode mount 118.

The lever 114 is pivotably mounted on hand-held portion 94 via lever tab 120 which is received within a mating opening in the tail section 122 of hand-held portion 94. The illustrated lever 114 is a hollow plastic structure defined by side walls 124, front wall 126 including slot 128 for receiving a rearward extension 130 of active electrode 90 and curved top 132. A pair of molded longitudinal protrusions 134 extend inwardly from side walls 124. These protrusions 134 are received about a narrowed portion of passive electrode mount 118, which is interconnected to passive electrode 92 and the lower extremities of the protrusions 134 abut against the beveled front edges 146 of active electrode mount 116 which is interconnected to active electrode 90.

Preferably, the active electrode 90 is biased towards the extended position for enhanced viewing during tissue engagement. This can be accomplished by urging the active electrode mount 116 towards a forward position. In the illustrated embodiment, a spring 136 is disposed between the tail section 122 of hand-held portion 94 and active electrode mount 116 to urge the mount 116 towards a forward position. The spring 136 extends around an alignment cylinder portion 138 and abuts against shoulder 140 of active electrode mount 116.

Thus, when no pressure is exerted on lever 114 by the surgeon, the spring 136 forces active electrode mount 116

(and active electrode 90) forward which in turn forces the lever 114 to a raised position due to the abutting relationship between protrusions 134 and the beveled front edges 146 of active electrode mount 116. The upward movement of lever 114 and, hence, the forward movement of active electrode 90 is ultimately limited by bulges 142, extending from the front wall 126 of lever 114 on both sides of slot 128, which abut against the top wall 144 of hand-held portion 94 when the active electrode 90 is in its fully extended position. Conversely, when the surgeon depresses the lever 114, the active electrode mount 116 and active electrode are moved rearwardly, eventually reaching the fully retracted position wherein the tip 106 of active electrode 90 is substantially nested within slit 110 of passive electrode 92.

In operation, the instrument can be used as follows. The elongated tubular portion 96 of housing 88 is inserted through an access cannula to the surgical site. The surgeon then moves the instrument axially and transversely relative to the access cannula and turns the swivel joint 100 as necessary to engage the tissue to be acted upon with the active electrode 90. The active electrode 90 is then pressed against the tissue to frictionally engage or slightly puncture the tissue thereby gripping the same. The tissue can then be drawn rearwardly to the passive electrode 92 by depressing lever 114. Transmission of an appropriate electrical signal from generator 82 is then initiated by activating a conventional foot or finger operated switch (not shown) to achieve the desired cutting, coagulation and/or desiccation effect. In this manner, a longitudinal incision can be formed through a series of such retract and cut motions.

It is an advantage of the present invention that a bipolar electrosurgical apparatus is provided wherein the return or passive electrode reliably maintains contact with tissue when the active electrode is positioned for surgery. It is a further advantage of the present invention that the return electrode can maintain tissue contact even in areas of irregular tissue topography. The present invention also provides a bipolar electrosurgical apparatus which is suitable for laparoscopic applications and which allows for enhanced viewing of the surgical site. It is a still further advantage of the present invention that a bipolar electrosurgical apparatus is provided which can function in a cut and in a coagulation mode for certain applications and can receive signals from generator outlets commonly associated with monopolar instruments. Moreover, the present invention allows for simple adjustment of cutting depth during surgery substantially without the need to interrupt surgery and limits the electrical current flow to a small tissue region. Further advantages will be apparent to those skilled in the art. The active electrode 90 is electrically interconnected to generator 82 via lead 108.

While the present invention has been described in relation to specific embodiments thereof, additional alternative embodiments apparent to those skilled in the art in view of the foregoing are intended to fall within the scope of the present invention as further defined by the claims set forth below.

What is claimed is:

1. A bipolar electrosurgical instrument for use in minimally invasive surgical procedures on internal portions of a patient's body, wherein access to said internal portions of said patient's body is obtained via an access cannula, said instrument comprising:

an instrument body including a rearward portion for handling by a user and an elongated forward portion for insertion through said access cannula;

active electrode means, extending forwardly from a front end of said forward portion of said instrument body, for transmitting electrical signals so as to produce electrosurgical effects adjacent to said active electrode means, said active electrode means including gripping means for gripping tissue adjacent to said active electrode means, wherein said active electrode means is capable of transmitting at least a first electrical signal for tissue cutting;

passive electrode means extending forwardly from said front end of said forward portion of said instrument body in closely spaced relationship relative to said active electrode means, said passive electrode means including a passive tissue contact surface having an area greater than that of an active tissue contact surface of said active electrode means, wherein said passive electrode means forms a portion of a circuit for transmitting said electrical signals substantially without producing electrosurgical effects adjacent to said passive electrode means; and positioning means for providing relative movement between said active electrode means and said passive electrode means after said active electrode means and said passive electrode means have been inserted through said access cannula, said positioning means operative for arranging said active electrode means and said passive electrode means between a first arrangement, wherein said active tissue contact surface and said passive tissue contact surface are separated by a first distance, and a second arrangement, wherein said active tissue contact surface and said passive tissue contact surface are separated by a second distance less than said first distance such that, during use, tissue can be gripped in said first arrangement and moved for cutting in said second arrangement.

2. The instrument of claim 1, wherein said positioning means provides for relative axial movement between said active electrode means and said passive electrode means between a first axially extended arrangement, wherein said active tissue contact surface is forwardly extended relative to said passive tissue contact surface, and an axially retracted position, wherein said active tissue contact surface is axially retracted relative to said passive tissue contact surface.

3. The instrument of claim 1, wherein said positioning means comprises actuation means mounted on said rearward portion of said instrument body for allowing a user to actuate said relative movement between said active electrode means and said passive electrode means.

4. The instrument of claim 1, wherein said positioning means comprises a lever mounted on said rearward portion.

5. The instrument of claim 1, wherein said active electrode means is moveable between an axially extended position and an axially retracted position relative to said passive electrode means, said instrument further comprising biasing means for urging said active electrode means towards said axially extended position.

6. The instrument of claim 1, wherein said gripping means comprises a hook for engaging tissue.

7. The instrument of claim 1, wherein said active electrode means comprises an axially extending portion and a transversely extending portion, said axially extending portion including an insulating material.

8. The instrument of claim 1, wherein said active electrode means is moveable between an axially extended position and an axially retracted position with respect to said passive electrode means, and said passive electrode means comprises a slot for receiving a portion of said active electrode means therein when said active electrode means is in said axially retracted position.

9. The instrument of claim 1, wherein said passive tissue contact surface is generally formed in the shape of a section of a sphere.

10. The instrument of claim 1, further comprising rotation means for allowing at least said active electrode means to rotate relative to said rearward portion of said instrument body.

11. The instrument of claim 1, further comprising swivel means for allowing said forward portion of said instrument body to swivel relative to said rearward portion of said instrument body.

12. The instrument of claim 1, further comprising electrical signal supply means capable of providing at least a first signal for cutting and a second signal for coagulation.

13. A bipolar electrosurgical instrument for use in minimally invasive surgical procedures on internal portions of a patient's body, wherein access to said internal portions of said patient's body is obtained via an access cannula, said instrument comprising:

an instrument body including a rearward portion for handling by a user and an elongated, substantially rigid forward portion for insertion through said access cannula;

active electrode means, extending forwardly from a front end of said forward portion of said instrument body, for transmitting electrical signals so as to produce electrosurgical effects adjacent to said active electrode means, said active electrode means including an active tissue contact surface;

passive electrode means extending forwardly from said front end of said forward portion of said instrument body in closely spaced relationship relative to said active electrode means, said passive electrode means including a passive tissue contact surface having an area greater than that of said active tissue contact surface, wherein said passive electrode means forms a portion of a circuit for transmitting said electrical signals substantially without producing electrosurgical effects adjacent to said passive electrode means; and positioning means for providing relative movement between said active electrode means and said passive electrode means after said active electrode means and said passive electrode means have been inserted through said access cannula, wherein said active electrode means and said passive electrode means are arrangeable in a first arrangement for positioning said electrosurgical instrument in preparation for an electrosurgical procedure and a second arrangement for conducting said electrosurgical procedure wherein said positioning means provides for relative axial movement between said active electrode means and said passive electrode means between a first axially extended arrangement, wherein said active tissue contact surface is forwardly extended relative to said passive tissue contact surface, and an axially retracted position, wherein said active tissue contact surface is axially retracted relative to said passive tissue contact surface.

14. The instrument of claim 13, wherein said active electrode means comprises a generally hook-shaped electrode for producing localized electrosurgical effects.

* * * * *